(12) United States Patent
Smith et al.

(10) Patent No.: US 9,867,611 B2
(45) Date of Patent: Jan. 16, 2018

(54) ANCHORING STUDS FOR TRANSCATHETER VALVE IMPLANTATION

(71) Applicant: St. Jude Medical, Cardiology Division, Inc., St. Paul, MN (US)

(72) Inventors: Kent J. Smith, Shoreview, MN (US); Peter N. Braido, Linwood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 672 days.

(21) Appl. No.: 14/462,729

(22) Filed: Aug. 19, 2014

(65) Prior Publication Data

US 2015/0066136 A1   Mar. 5, 2015

Related U.S. Application Data

(60) Provisional application No. 61/873,899, filed on Sep. 5, 2013.

(51) Int. Cl.
*A61F 2/24* (2006.01)
*A61B 17/064* (2006.01)

(52) U.S. Cl.
CPC .......... *A61B 17/064* (2013.01); *A61F 2/2409* (2013.01); *A61F 2/2445* (2013.01);
(Continued)

(58) Field of Classification Search
CPC ........... A61B 17/064; A61B 2017/0647; A61F 2/2445; A61F 2250/0063; A61F 2250/006;
(Continued)

(56) References Cited

U.S. PATENT DOCUMENTS 3,657,744 A   4/1972  Ersek
4,275,469 A   6/1981  Gabbay
(Continued)

FOREIGN PATENT DOCUMENTS

DE   19857887 A1   7/2000
DE   10121210 A1   11/2002
(Continued)

OTHER PUBLICATIONS

Catheter-implanted prosthetic heart valves, Knudsen, L.L., et al., The International Journal of Artificial Organs, vol. 16, No. 5 1993, pp. 253-262.
(Continued)

*Primary Examiner* — Richard Louis
(74) *Attorney, Agent, or Firm* — Lerner, David, Littenberg, Krumholz & Mentlik, LLP

(57) ABSTRACT

An anchoring device for use within a vascular structure includes a head having a first surface and a second surface meeting at a common plane, and an anchor including a shaft having a longitudinal axis, a first end connected at a junction to the first surface of the head, and a free end. A harbor space is bounded by the shaft of the anchor, the first surface of the head, a first theoretical plane perpendicular to the longitudinal axis at a spaced distance from the junction and a second theoretical plane tangential to the head at a point in the common plane. The harbor space has an are sufficient to receive a portion of a stented device therein.

10 Claims, 15 Drawing Sheets

(52) U.S. Cl.
CPC ..... *A61B 2017/0647* (2013.01); *A61F 2/2412* (2013.01); *A61F 2220/0033* (2013.01); *A61F 2250/006* (2013.01); *A61F 2250/0063* (2013.01)

(58) Field of Classification Search
CPC ............ A61F 2220/0033; A61F 2/2412; A61F 2/2409
See application file for complete search history.

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,986,786 B1 * | 1/2006 | Smith | A61F 2/07 623/1.13 |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 2002/0036220 A1 | 3/2002 | Gabbay | |
| 2003/0009174 A1 * | 1/2003 | Smith | A61F 2/966 606/108 |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2003/0167089 A1 * | 9/2003 | Lane | A61F 2/2412 623/2.14 |
| 2003/0216807 A1 * | 11/2003 | Jones | A61B 17/12022 623/1.22 |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0240263 A1 * | 10/2005 | Fogarty | A61B 17/0401 623/2.38 |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0136052 A1 * | 6/2006 | Vesely | A61F 2/2412 623/2.18 |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0150053 A1 * | 6/2007 | Gurskis | A61F 2/2409 623/2.38 |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0004696 A1 * | 1/2008 | Vesely | A61F 2/2418 623/2.1 |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0125095 A1 * | 5/2009 | Bui | A61F 2/07 623/1.13 |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |

(56) References Cited

U.S. PATENT DOCUMENTS

| | | |
|---|---|---|
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0283514 A1* | 11/2011 | Fogarty ............ A61B 17/0401 29/428 |
| 2012/0203332 A1* | 8/2012 | Navia ................ A61F 2/2427 623/2.11 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 10008549 A1 | 1/2010 |
| WO | 10096176 A1 | 8/2010 |
| WO | 10098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR, dated May 25, 2010.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology (1998) 7:102-106 (1998).
Transluminal implantation of artificial heart valves, Andersen, H. R., et al., European Heart Journal (1992) 13, 704-708.

* cited by examiner

ANCHORING STUDS FOR TRANSCATHETER VALVE IMPLANTATION

CROSS-REFERENCE TO RELATED APPLICATION

The present application claims the benefit of the filing date of U.S. Provisional Patent Application No. 61/873,899 filed Sep. 5, 2013, the disclosure of which is hereby incorporated herein by reference.

BACKGROUND OF THE INVENTION

Heart valve disease may either be congenital or develop over a period of time and often materializes without notice. Where possible, patients are monitored and instructed to make lifestyle changes. However, where the function of the valve becomes significantly impaired, the only option may be heart valve replacement or repair.

There are two general types of heart valve replacement procedures. The first type is surgical replacement where the patient is placed on a heart and lung machine to undergo open heart surgery. The heart is stopped so that the diseased valve may be surgically removed and replaced by a prosthetic valve sutured into the same general location. This type of procedure is often the first consideration because of its long-term efficacy. However, open heart surgery is highly invasive and includes many attendant risks with the potential to be very severe or life threatening. Aside from the physical trauma of invading one of the most crucial areas of the human body, the risks are compounded by the heart and lung machine, which, among other things, can damage red blood cells leading to neurological deficiencies.

Due to these attendant risks, surgical valve replacement may not be a viable option, particularly for the elderly and frail. Additionally, individuals who receive surgical replacements earlier in life may need to have a follow-up replacement, which would likely be performed at an age where open heart surgery may be too risky. Thus, transcatheter valve implantation may be the best approach as the other type of heart valve replacement procedure. Transcatheter valve implantation is generally achieved by guiding a catheter, which retains an expandable prosthetic valve, through a patient's cardiovascular system to the diseased valve. The prosthetic valve is deployed such that the diseased valve is pushed out of the way so that the prosthetic valve can take over. Expandable prosthetic valves are primarily comprised of porcine or bovine tissue that is sewn to a stent that includes struts forming individually expandable cells. The stent may be made from a memory metal material, such as Nitinol, which gives it a natural bias toward an expanded state in order to hold the prosthetic valve in place.

Transcatheter valve implantation is currently indicated only for patients with severe stenosis. The primary reason for this limitation is valve migration. While the natural bias of the stent helps exert significant radial force against the surrounding soft tissue, this radial force typically is not enough to counteract the force of the flow of blood and gyrations from the beating heart. Thus, transcatheter valve implantation is indicated only for severe cases of stenosis so that the stent has a stable anchoring structure, such as calcium build-up, along the soft tissue of the native heart valve.

Consequently, there is a large segment of individuals who suffer from a valvular disease that requires valve replacement but who may not qualify for surgical replacement or transcatheter valve implantation. Therefore, there is a need for technology that would provide a stable anchoring platform for a transcatheter valve prosthesis in order to address the problem of migration so that a wider array of individuals may be effectively treated.

BRIEF SUMMARY OF THE INVENTION

Generally, the present disclosure includes devices and methods for use in anchoring a transcatheter valve prosthesis in situ. More specifically, the disclosure relates to an anchoring device for use within a cardiovascular structure, including a coronary annular and/or valvular structure. The anchoring device includes a head having a first surface and a second surface meeting at a common plane. The anchoring device also includes a shaft having a first end connected at a junction to the first surface of the head, and a free end. The shaft has a longitudinal axis between the first end and the free end. Further, the anchoring device includes a harbor space bounded by the shaft of the anchor, the first surface of the head, a first theoretical plane that is perpendicular to the longitudinal axis at a spaced distance from the junction, and a second theoretical plane that is tangential to the head at a point in the common plane. The harbor space includes an area sufficient to receive a portion of a stented device.

Another aspect of the present disclosure relates to a valvular prosthesis for use within a vascular structure, which includes a first prosthesis body. The first prosthesis body includes an outer portion for engagement with tissue within the vascular structure and an inner portion disposed opposite the outer portion. The valvular prosthesis also includes an anchoring device attached with the first prosthesis body. The anchoring device includes a head extending away from the inner portion of the first prosthesis body. The head defines a junction area with the first surface adjacent or on the first prosthesis body, and a first face that extends away from the junction area and longitudinally away from the first prosthesis body.

Another aspect of the present disclosure relates to a method of anchoring a stented device. The method includes the step of guiding a catheter to a deployment location within the cardiovascular system of a patient. The catheter contains therein, in a contracted configuration, an expandable stented device that includes a plurality of individually expandable cells. The deployment location includes at least one anchoring device with a head projecting radially inwardly within the deployment location. The method also includes the step of removing the stented device from the catheter within the deployment location. Additionally, the method includes expanding the stented device such that the head of the anchoring device extends through one of the cells of the stented device.

BRIEF DESCRIPTION OF THE DRAWINGS

These and other features, aspects, and advantages of the present invention will become better understood with regard to the following description, appended claims, and accompanying drawings in which:

DETAILED DESCRIPTION

The following description generally pertains to an anchoring device that can be used in connection with a transcatheter valve prosthesis. Multiple valves exist in the cardiovascular system of the human body including the heart and veins. It is to be understood that the anchoring device described herein may be utilized for any sutureless surgical valve or any valve replacement performed via catheter including, but not limited to, implantation of a Portico® Transcatheter Aortic Valve (St. Jude Medical, Inc., St. Paul, Minn.). Further, such anchoring device may accommodate a transcatheter valve prosthesis delivered via any delivery approach including, but not limited to, trans-femoral, trans-apical, trans-aortic and subclavian approaches. Also, while the use of an anchoring device is described herein with reference to valvular prostheses, it is to be understood that the anchoring devices may also be utilized in conjunction with general purpose stents other than for valve replacement. The term "vascular structure" as used herein can be any cardiovascular structure including a coronary annular and/or valvular structure.

Figure 2:
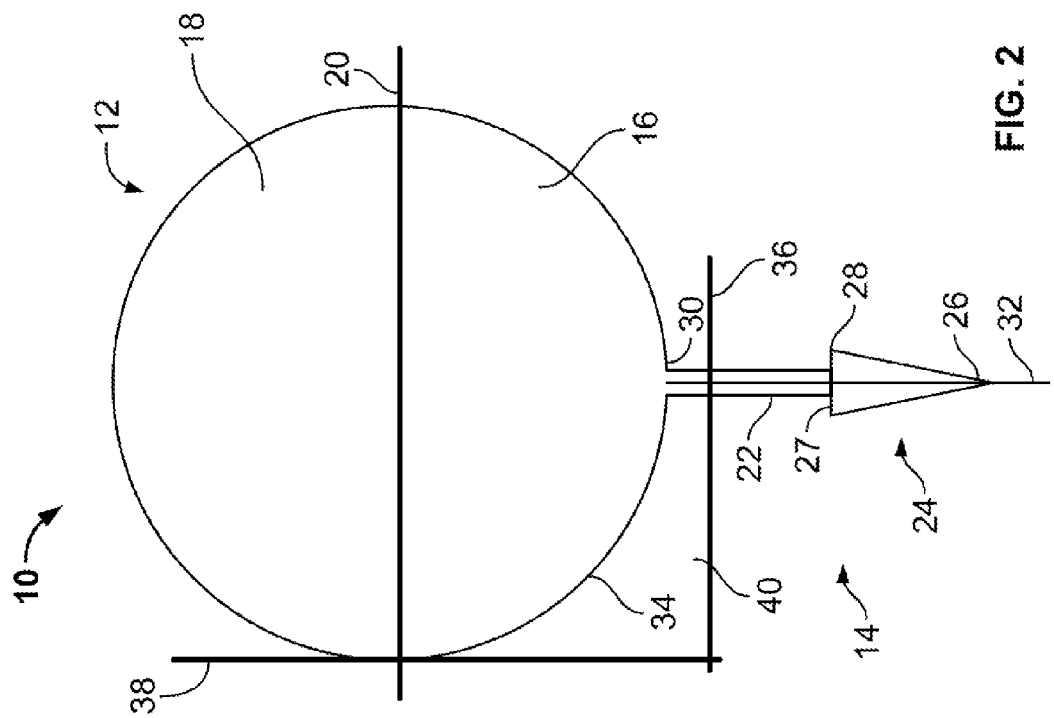
FIG. 2 is a front view of the anchoring device of FIG. 1 defining a harbor space for receipt of a portion of a transcatheter prosthesis.
Figure 1:
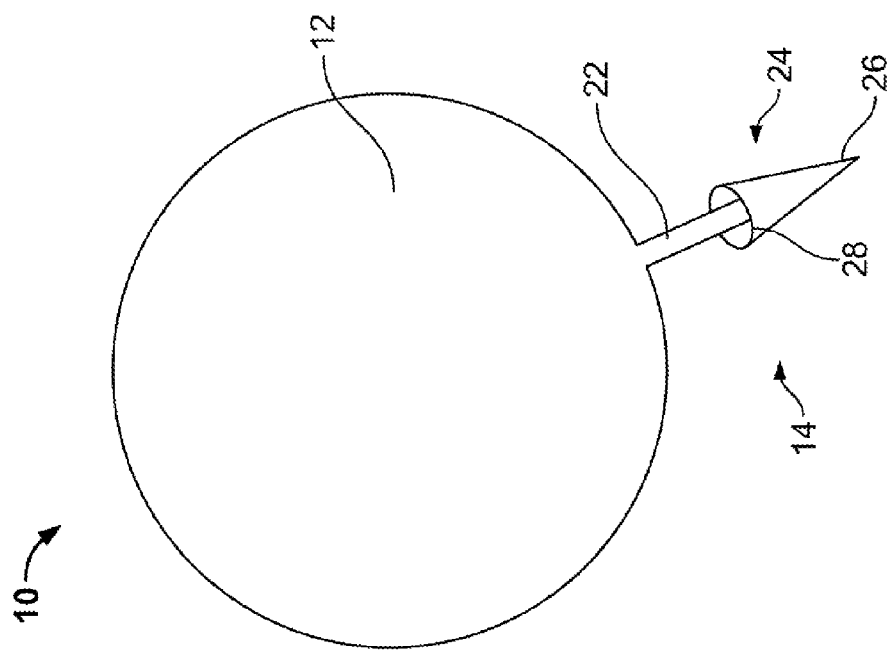
FIG. 1 is a perspective view of an anchoring device having a first embodiment of a head and a first embodiment of an anchor.

FIGS. 1-2 depict a first embodiment of an anchoring device 10 for use within a cardiovascular structure, for example, the aorta or portions of the heart adjacent the aorta. The anchoring device 10 may be utilized to provide a solid anchoring platform for a transcatheter valve prosthesis in order to prevent valve migration, as discussed further below. The anchoring device 10 generally includes a head 12 and an anchor 14.

The anchoring device 10 may be made from any biocompatible material including, but not limited to, pyrolytic carbon, stainless steel, nickel-titanium alloy (commonly referred to as "Nitinol") and biocompatible polymers. Anchoring device 10 may also be made from a radiopaque material or include a radiopaque filler. Alternatively, the anchoring device 10, or at least the anchor 14, may be bio-absorbable, hydrophilic, Nitinol expandable foam, polymer inflated, or cloth covered to facilitate in-growth and/or reduction of flow disruption over time.

As shown, head 12 may be substantially spherical, and includes a first side 16 and a second side 18, which converge at an equator 20 of the spherical profile. As used herein, the term "equator" of head 12 means a theoretical line that encircles head 12 along a plane perpendicular to an axis of head that passes through the center of head 12 and through junction area 30, the plane being positioned along the axis of head 12 so as to equally divide the head 12 between the first side 16 and the second side 18. While the head 12 is depicted as spherical, the head may take on various other shapes and configurations, such as (but not limited to) a disc, a toroid, or a polygon, for example.

Anchor 14 may include a shaft 22 and a mooring feature 24. Shaft 22 may have a generally constant cross-sectional area along its length or may be tapered along its length. Further, shaft 22 may be generally straight or curved along its length. Mooring feature 24 may be in the form of an inverted cone, as substantially shown, and may be coupled to one end of shaft 22 either through a mechanical connection or through manufacture as a monolithic structure. At its free end, mooring feature 24 may have a point 26 sufficiently sharp to penetrate soft tissue.

The combined length of shaft 22 and mooring feature 24 may be sufficiently long to enable point 26 of mooring feature to at least partially penetrate the vascular tissue, but short enough that point 26 does not penetrate all the way through the vascular wall. In other words, the combined length of shaft 22 and mooring feature 24 is preferably less than the thickness of the vascular wall to which anchoring device 10 is to be applied.

Opposite point 26, mooring feature has a widened surface 27 where it joins shaft 22. Surface 27 may be recessed so as to define a narrow edge 28 around its periphery. Edge 28 may be sharpened or may have gripping features to prevent mooring feature 24 from backing out from the tissue once it has been implanted. An example of one such gripping feature may be a plurality of sharpened tabs (not shown) disposed along edge 28 and pointing in a direction opposite point 26. Such tabs may be biased radially outwardly and may be flexible such that they do not hinder insertion of mooring feature 24 into the vascular structure. However, when mooring feature 24 is subjected to a force in a direction away from the tissue, the tabs may grip the soft tissue and splay outwardly to prevent both backing out of anchoring device 10 and excessive damage to the vascular structure.

Referring to FIG. 2, anchor 14 may be connected to first side 16 of head 12 at a junction area 30. Junction area 30 may include a mechanical connection between head 12 and anchor 14, such as a threaded connection, a welded connection, a press fit connection, or other types of mechanical connections known in the art. Alternatively, head 12 and anchor 14 may be formed during the manufacturing process as a unitary structure. Anchor 14 may extend along a longitudinal axis 32 that intersects with head 12 at junction area 30 at either a perpendicular angle or an oblique angle.

The first side 16 of head 12 also defines a harbor portion 34 that extends away from junction area 30. Harbor portion 34 generally is an area of head 12 that may engage, along with adjacent tissue to which device 10 is anchored, a portion of a strut of a transcatheter valve.

FIG. 2 also depicts a harbor space 40 that is a space defined by a first theoretical plane 36, a second theoretical plane 38, and harbor portion 34. While harbor portion 34 may engage a strut, harbor space 40 is the region in which the portion of the strut generally resides when the valve prosthesis is fully implanted within the vascular structure. Harbor space 40 may span an entire 360 degrees about anchoring device 10 to capture a strut from any direction.

First theoretical plane 36 may be oriented perpendicular to longitudinal axis 32 and intersecting anchor 14 at any point between junction area 30 and point 26. Second theoretical plane 38 may be oriented tangent to head 12 at its equator 20. Planes 36 and 38 may intersect one another at a right angle or at an oblique angle. As an example, where head is not symmetric, second theoretical plane 38 may not be parallel to longitudinal axis 32 when tangent to equator 20. Thus, even if first theoretical plane 36 is orthogonal to longitudinal axis 32, the angle of intersection between planes 36 and 38 may be oblique. Similarly, where anchor 14 extends from head 12 such that longitudinal axis 32 is oblique to junction area 30, the angle of intersection between planes 36 and 38 may be oblique even if second theoretical plane 28 is in a completely vertical orientation.

Figure 3A:
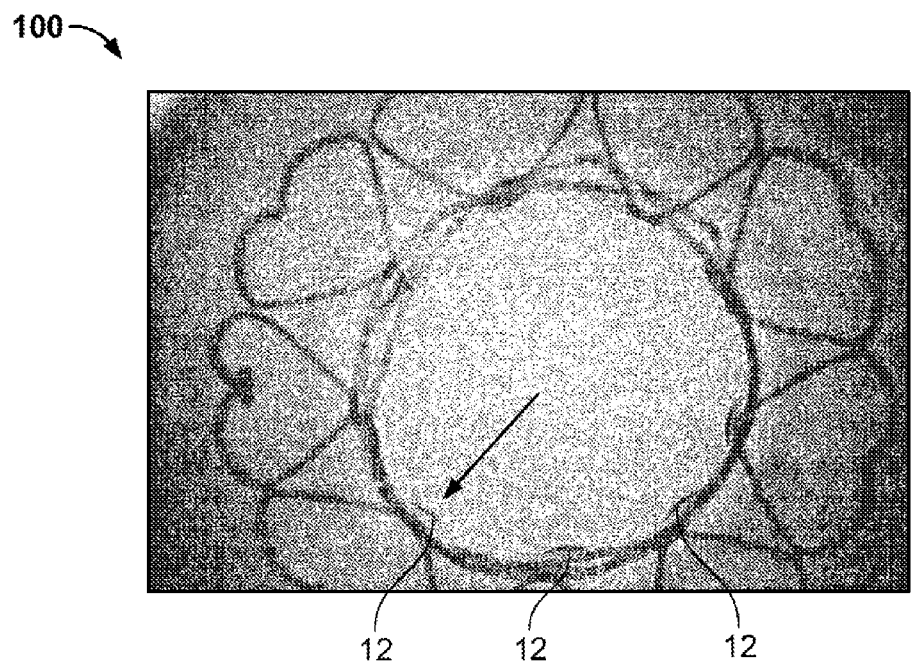
FIG. 3A is a radiographic image depicting a plurality of anchoring devices in an implanted state relative to a transcatheter valve prosthesis.
Figure 3B:
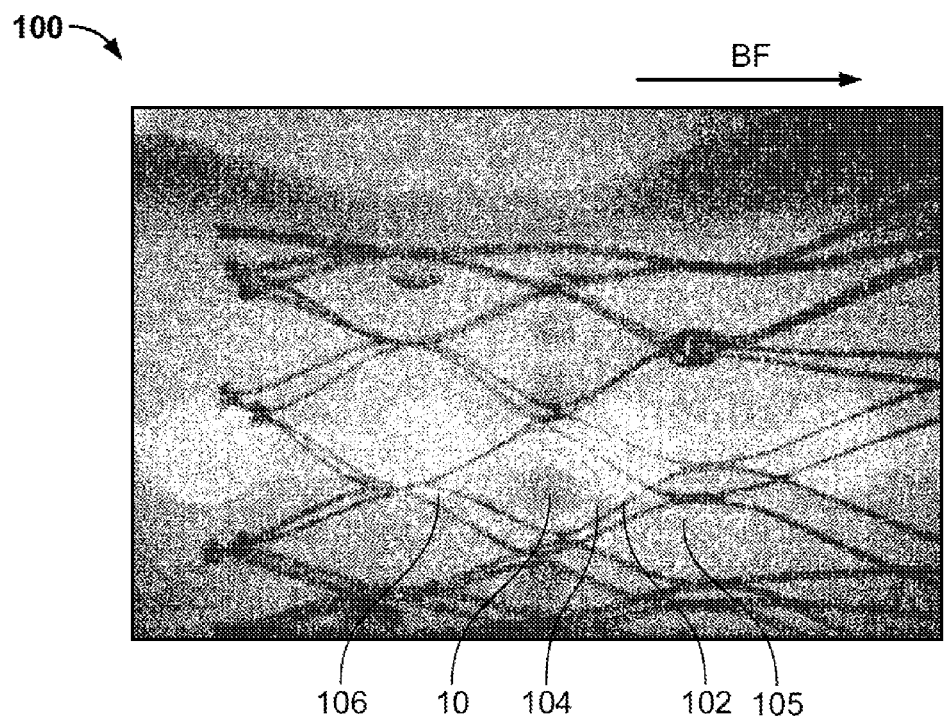
FIG. 3B is another radiographic image depicting a plurality of anchoring devices in an implanted state relative to a transcatheter valve prosthesis.

FIGS. 3A and 3B are radiographic images illustrating a transcatheter valve 100 anchored in place by anchoring device 10. FIG. 3A illustrates how head 12 may be smaller in size than an individual cell 104 formed by struts 102 so that head 12 extends through cell 104.

Struts 102 of transcatheter valve 100 form a generally diamond-shaped cell 104 such that vertices 105 and 106 of cell 104 are generally aligned with the flow of blood. Migration of valve 100 may typically occur in the direction of blood flow (in the direction of arrow BF in FIG. 3B) or in the opposite direction of blood flow when the valve is closed and subject to backpressure. Thus, as the valve migrates toward anchoring device 10, the narrow section of struts 102 near vertex 105 or 106 becomes captured within harbor space 40 of anchoring device 10. As the struts are captured within harbor space 40 and push against shaft 14, the migratory forces are opposed by the resistance provided by the firmly positioned anchoring device 10, effectively anchoring the transcatheter valve in place.

Anchoring is further enhanced by head 12. Head 12 may have a cross-sectional area larger than that of shaft 14, thereby forming an overhang. This overhang may be sized such that individual struts captured within harbor space 40 and nearly abutting shaft 14 are completely covered above by the overhang of head 12. This overhang effectively prevents struts 102 from jumping over anchoring device 10.

FIGS. 3A and 3B also demonstrate that multiple anchoring devices 10 may be implanted and may extend through various cells 104 of transcatheter valve 100. Should the anchoring devices 10 be positioned all the way around the circumference of the transcatheter valve 100, they can be easily positioned at different locations among the various cells 104 of the valve. As such, the anchoring devices 10 can be positioned to restrict movement of the valve 100 in various directions. By doing so, the position of the valve 100 can be further maintained within the native valve structure.

Figure 4:
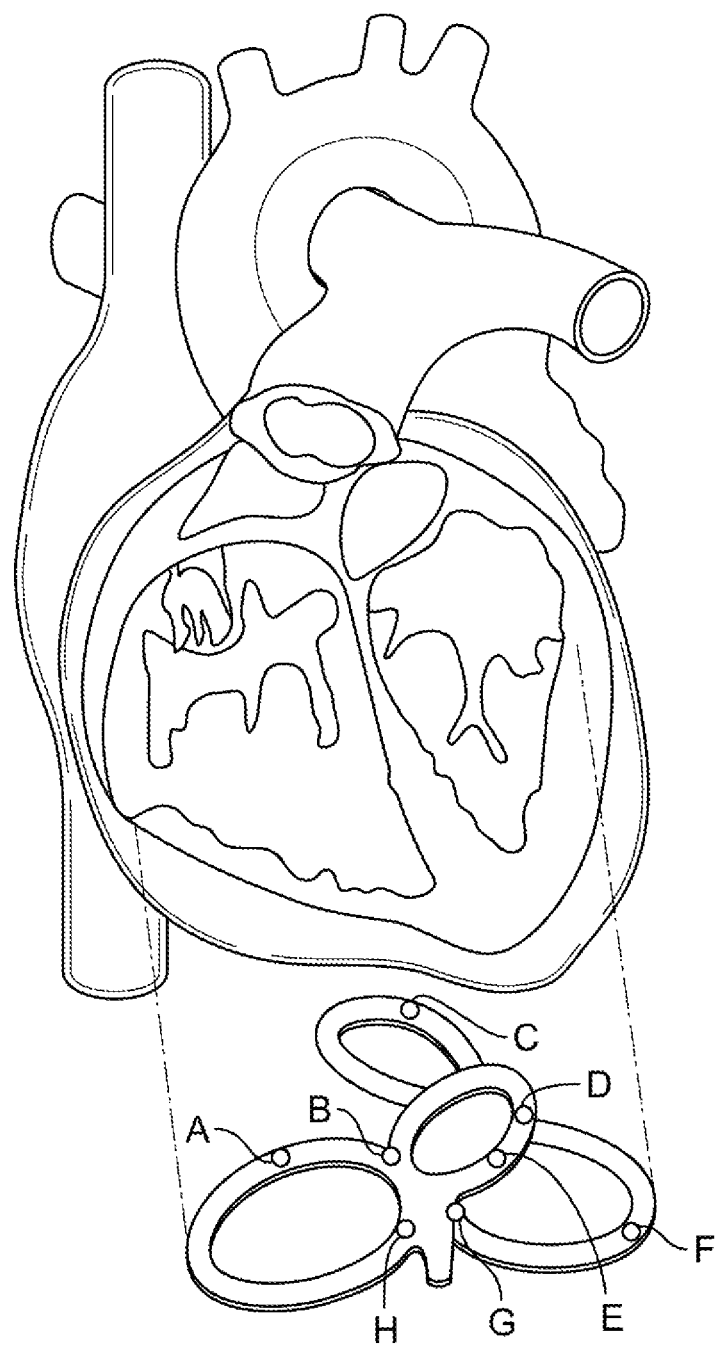
FIG. 4 is a highly schematic view of the heart, with a projection showing the configuration of heart valves and potential implant locations for the anchoring device within the configuration.

FIG. 4 shows a schematic projection view of the annuli of the semilunar and atrioventricular valves including examples of various implant locations A-H within the heart in which anchoring devices 10 may be implanted. At these particular positions, anchor 22 may engage the native annulus or leaflets of the native valve, which may include the mitral valve, tricuspid valve, aortic valve, and pulmonary valve. However, these locations are merely examples and have been selected to demonstrate that anchoring devices 10 could engage adjacent muscular tissue and avoid shared vascular walls and other structures such as the atrioventricular node ("AV") node. Additionally, anchoring device 10 can be implanted outside of the native valve annulus, for example, in the sinotubular junction, aorta, atria, and septum as needed to account for specific patient characteristics such as porcelain aorta.

While the figures depict individual locations for anchoring device 10, it is possible to utilize multiple anchoring devices 10 for one transcatheter valve prosthesis, as shown in FIGS. 3A and 3B. In such an instance, anchoring devices 10 may be implanted in ring, spiral or discrete sectional configurations to match the patient's heart anatomy and the transcatheter valve geometry. As such, where multiple anchoring devices 10 are implanted, the anchoring devices 10 may be in a predetermined spatial relationship configured to match the size and spacing of the individual cells 104 formed by the struts 102 of the transcatheter valve 100. For example, each anchoring device 10 may be spaced from each other so that when transcatheter valve 100 is expanded within the vascular structure, each anchoring device 10 extends into a separate stent cell 104 without interfering with the full expansion of the valve 100 and without forcing a stent strut 102 to bend to avoid the anchoring device in order for the stent to achieve full expansion. It is even contemplated that anchoring devices 10 may be spaced in such a way that where the expansion of transcatheter valve 100 is initially interfered with by the abutment of a strut 102 against the head of one anchoring device 10, then the remaining anchoring devices 10 will be abutted by another strut 102 at another location around the circumference of the transcatheter valve 100. In such a situation, the roundness of the head 12 and radial positioning of all of the anchoring devices 10 can push the struts 102 and rotate the transcatheter valve 100 so that expansion interference is mitigated and structural deformation of the strut 102 does not need to occur to resolve the interference.

While it is preferable to predetermine the spatial configuration of the anchoring devices 10, in some circumstances it may not be possible or practicable. In such circumstances, anchoring devices 10 may deform the stent where the spacing does not result in an exact fit but be sized to deform the stent in the same fashion as naturally occurring calcific nodules would deform the stent. Additionally, the anchoring devices may be sized to maximize the possibility of fitting within the stent cell and to mitigate or eliminate any paravalvular leaks.

Aside from being implantable into the native annulus or native valve leaflet, anchoring device 10 may also be implanted into a prosthetic valve that previously had been implanted for a valve-in-valve ("V-in-V") implantation configuration. Furthermore, a prosthetic valve may initially (i.e., prior to its own implantation) include an anchoring device (not shown) in anticipation of a future "V-in-V" implantation. Such anchoring devices utilized for V-in-V implantation may be attached to a prosthetic valve during the manufacturing process, for example, via suture, glue, heat bonding or built continuously with a stent.

FIGS. 5-9B depict various locations at which anchoring devices can be placed on a surgical valve assembly or mitral valve repair device. Such placement can be done during a transcatheter V-in-V procedure, prior to implantation of the second valve. Additionally or alternatively, an anchoring device can be assembled with a prosthetic valve during its manufacturing process.

Figure 5:
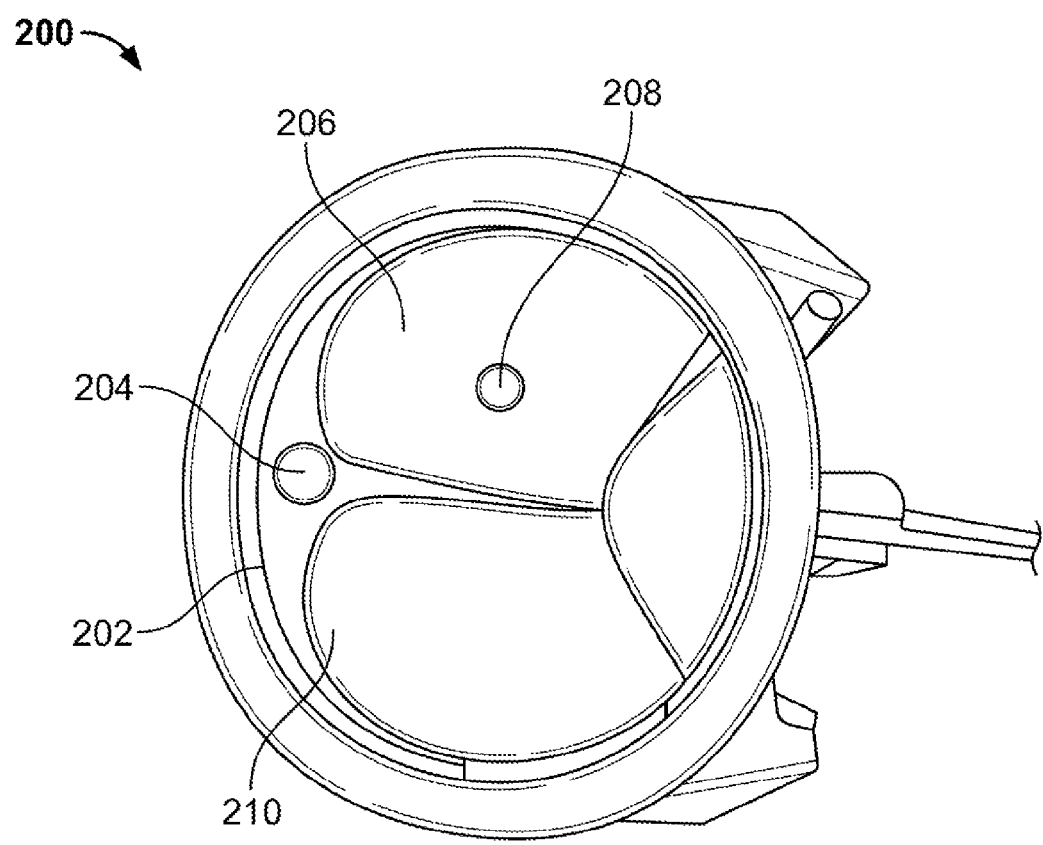
FIG. 5 is a perspective view of a surgical valve prosthesis depicting potential anchoring device locations for anchoring a transcatheter valve thereto.

Referring to FIG. 5, a surgical replacement valve 200 is shown, in particular the Trifecta® heart valve (St. Jude Medical, Inc., St. Paul, Minn.). In such a valve, anchoring device 10 may be implanted into either cuff 202, as shown by point 204, or leaflet 206, as shown by point 208. An anchoring device (not shown) may also be built into valve 200 at these locations during the manufacturing process. This may be achieved by sewing the anchoring device into the bioprosthetic or synthetic material of the valve prosthesis, and the analog device may include a modified version of anchor 14 that may include a ring, opening, or other feature that can be used to suture the device to valve 200.

Where an anchoring device is built into a surgical valve prosthesis, a transcatheter valve prosthesis, or an annuloplasty ring, the principle for forming a harbor space to retain a strut of a transcatheter valve remains relatively the same as in examples wherein an anchoring device is later implanted. The anchoring device, or alternatively termed an "anchoring protrusion," may similarly include a head, such as that in FIGS. 1-2, and a mating portion for mating with the prosthesis. The mating portion may be adapted to securely connect to the valve prosthesis, for example, with a sewn connection. The mating portion, as with the anchor described previously, may extend from a point at which it joins the head along a longitudinal axis, and may form a harbor space between a harbor portion of the head and the inner surface of the valve prosthesis in substantially the same manner as described previously. In some embodiments, the head may be a hook-like structure (not shown) for mating with a receiving feature built into later implanted valve prosthesis. Such a feature may provide for uni-directional locking so that a later-implanted valve prosthesis may be resheathed from the locked position.

Figure 6A:
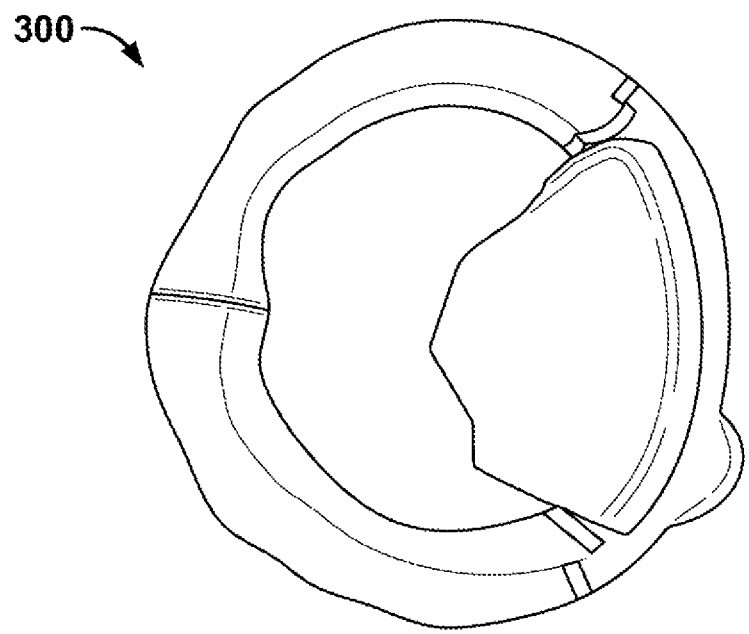
FIGS. 6A and 6B are end views of surgical valve prostheses depicting potential anchoring device locations for anchoring a transcatheter valve thereto.
Figure 6B:
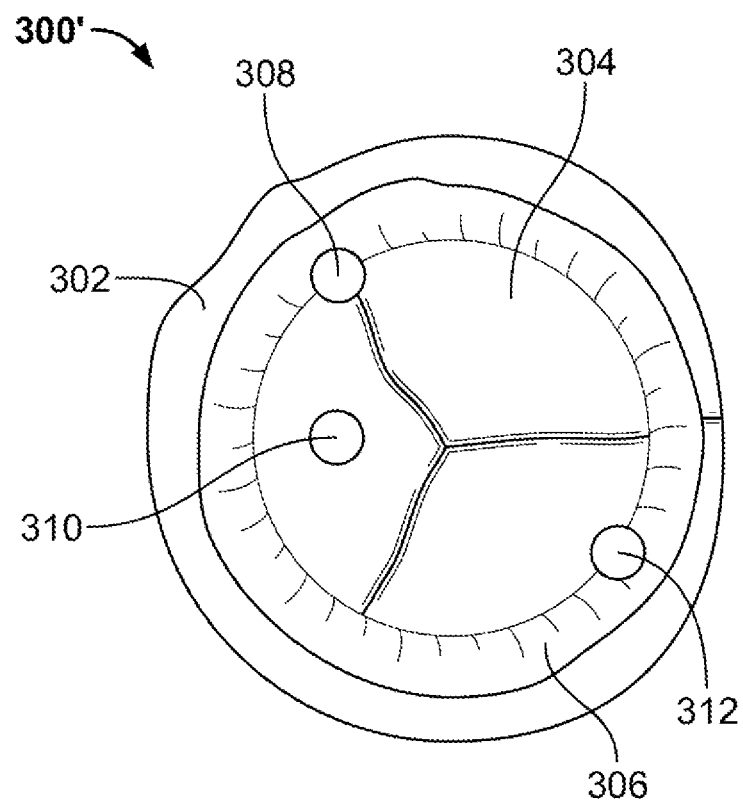

Similarly, an anchoring device may either be implanted into or built into prosthetic valves 300 or 300', as shown in FIGS. 6A and 6B. FIG. 6A depicts a surgical mitral valve prosthesis 300 and FIG. 6B depicts a surgical aortic valve prosthesis 300' similar to those within the SJM Biocor® and SJM Epic® heart valve families (St. Jude Medical, Inc., St. Paul, Minn.). As shown in FIG. 6B, an anchoring device may be implanted or built into the prosthetic valve 300' such that the head thereof is positioned on a leaflet or over portions of a pair of leaflets with the anchor thereof extending through a leaflet. In an example, the anchor of an anchoring device may extend into and engage with the corresponding leaflet 304 alone at location 310. In other examples, the anchor of an anchoring device may further extend into and engage with or be affixed with cuff 302 with the head thereof in location 308, or the anchor of an anchoring device may further extend into and engage with or be affixed with tissue annulus 306 with the head thereof in location 312. As has been described, an anchoring device can be positioned in one or more of the positions illustrated 308, 310, and 312 and may be sewn into the valve prosthesis during the manufacturing process. Further, it is noted that the illustration of FIG. 6B, is exemplary and is intended to show possible positions for anchoring devices in prosthesis 300'. Other examples can include a single anchoring device in any of the positions shown, or multiple anchoring devices in similar or different positions and attached in the same, similar, or different structures of prosthesis 300'.

Figure 7B:
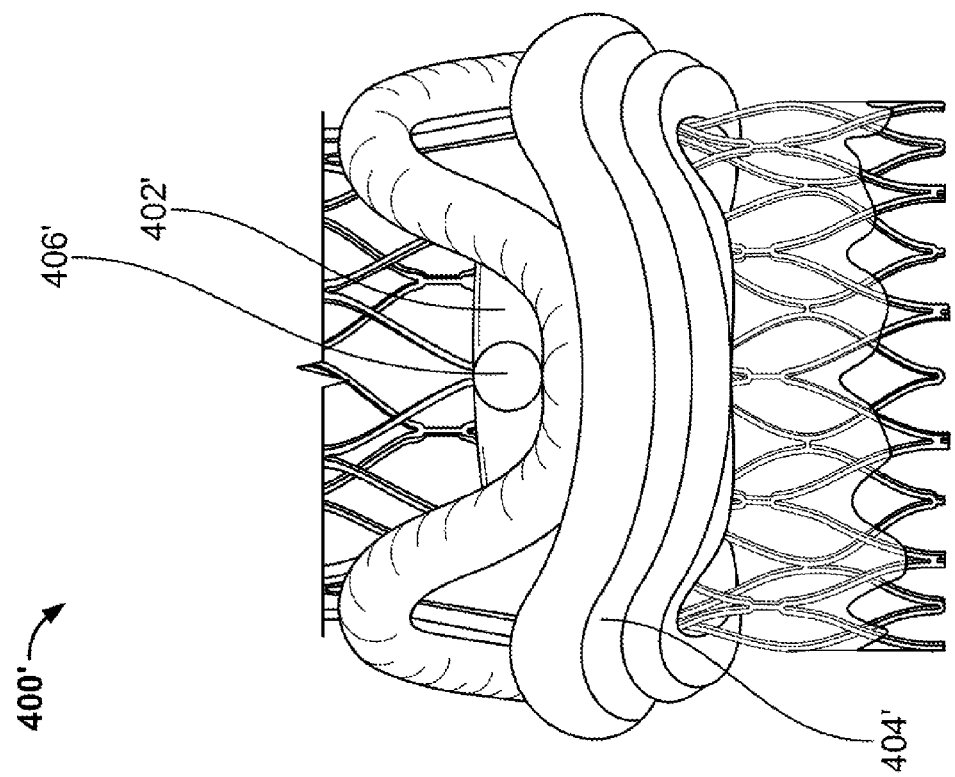
FIG. 7B is a side view of a transcatheter valve prosthesis in a low positioning configuration within a surgical valve and depicting potential anchoring device locations for valve-in-valve implantation.
Figure 7A:
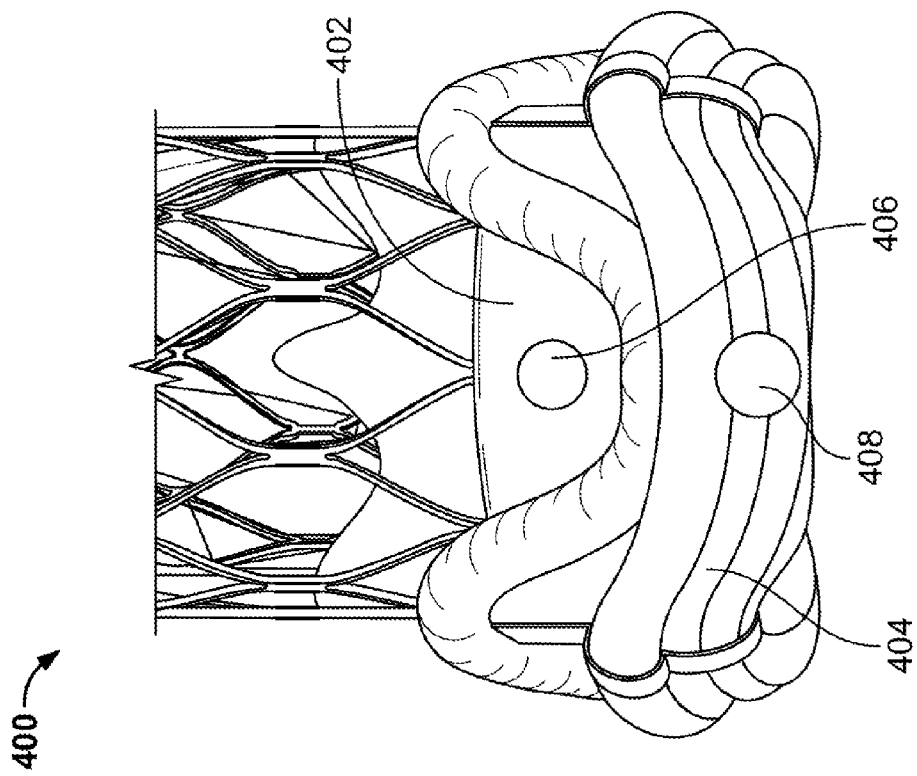
FIG. 7A is a side view of a transcatheter valve prosthesis in a high positioning configuration within a surgical valve and depicting potential anchoring device locations for valve-in-valve implantation.

FIGS. 7A and 7B illustrate a transcatheter valve prosthesis in a V-in-V configuration with a surgical valve prosthesis, namely a Portico® transcatheter valve within a Biocor® surgical valve (both from St. Jude Medical, Inc., St. Paul, Minn.). As shown in FIGS. 7A and 7B, various configurations of the anchoring devices used can accommodate various positioning of the second replacement (or inner) valve. In the example of FIG. 7A, a "high" positioning is depicted for inner valve 400 wherein inner valve 400 is positioned relative such that the annulus section thereof is positioned within the cuff 404 of the outer valve. In such a configuration 400, an anchoring device may be implanted or built into the outer valve leaflet 402 at depicted location 406 and/or in the outer valve cuff in the inflow region of the outer valve at depicted location 408. In the high positioning configuration, large outward forces of the annulus section of inner valve 400 may allow the use of only one anchoring device.

Alternatively, FIG. 7B depicts a "low" positioning configuration wherein the second replacement valve 400' is positioned such that a portion of the annulus section of valve 400' extends outside of cuff 404' of the first replacement valve. In such an example, an anchoring device may be implanted or built into the surgical valve leaflet 402' at depicted location 406'. Additionally, an anchoring device may be implanted or built into the cuff or annulus of the first replacement valve. In the low positioning configuration, the first valve may be positioned along a region of valve 400' that has larger stent cells and, as such, may be subject to larger pulsing strut motion compared to smaller stent cells. Thus, it may be desirable to utilize multiple anchoring devices in the low positioning configuration.

Figure 8:
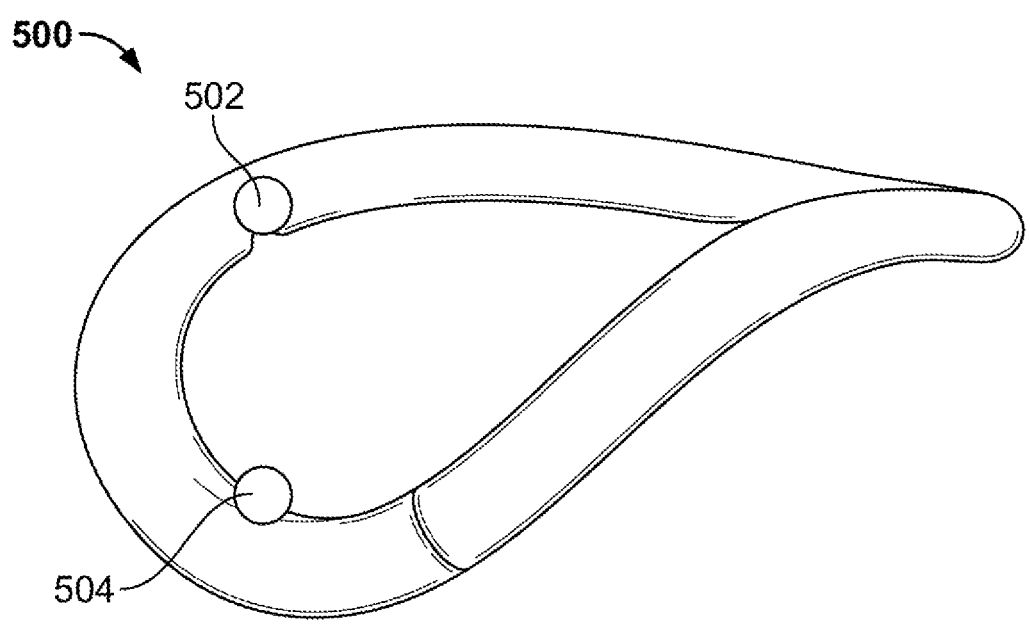
FIG. 8 is a perspective view of an annuloplasty ring depicting potential anchoring device locations.

An anchoring device may also be utilized in a quasi-V-in-V implantation following repair of a damaged mitral valve utilizing an annuloplasty ring 500. FIG. 8 depicts an annuloplasty ring 500 with pre-placement locations 502 and 504 for one or more anchoring devices (not shown). The ring 500 can include a fabric covering over a rigid or stiff core that gives the ring 500 its shape. When the anchoring device(s) is placed during manufacture of the annuloplasty ring 500, the anchoring device may be sewn into the inside diameter of the ring, through the outer fabric, for example, or can be attached to the core of the ring. Either mode of attachment can be done using sutures or a modified anchor that is adapted to engage the core of ring 500.

Figure 9A:
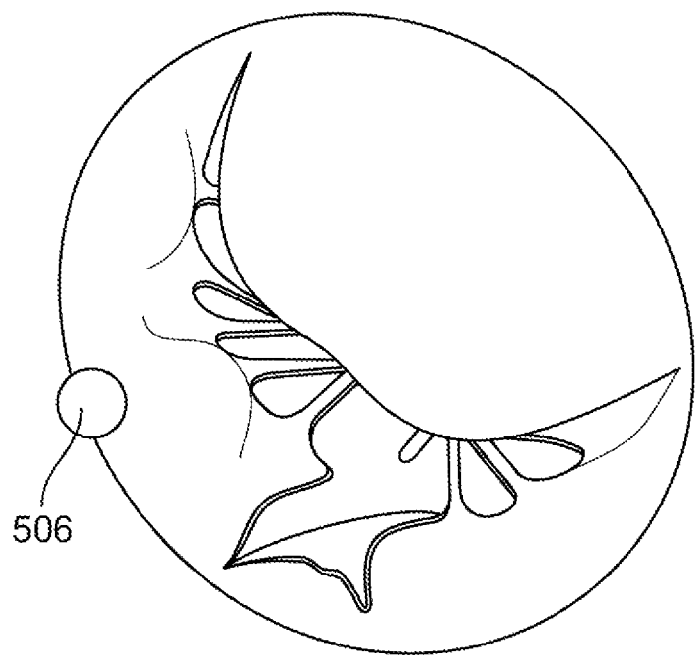
FIG. 9A is an end view of a torn mitral valve depicting an anchoring device implantation location.
Figure 9B:
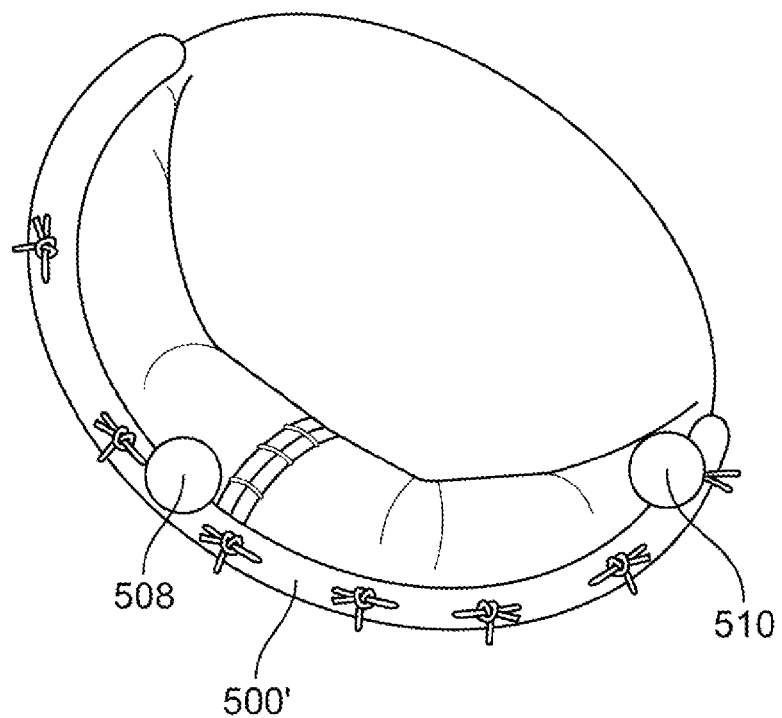
FIG. 9B is an end view of a repaired mitral valve depicting potential anchoring device locations.

FIG. 9A demonstrates that when a damaged mitral valve is being replaced rather than repaired, the implant location of anchoring device 10 may be in the native valve annulus, as demonstrated by point 506. In FIG. 9A, the anchoring device (not shown) can be immediately used to help secure the position of the replacement valve that is to be implanted during the same procedure. FIG. 9B illustrates possible positions 508 and 510 for anchoring devices that can be used to secure the position of a replacement valve that is implanted after the mitral valve has been previously repaired utilizing an annuloplasty ring 500'. In an example, the anchoring devices used can be implanted into locations 508 and 510 during the procedure for implantation of the replacement valve and can be implanted into the native valve annulus tissue in location 510 or can be implanted into the annuloplasty ring 500' in location 508. Alternatively, the anchoring devices may be built into the annuloplasty ring 500' before the implantation thereof during the annuloplasty procedure. Such annuloplasty ring 500' may be unused for some time, i.e., while the repaired mitral valve functions normally. Should the patient outlive the viability of the repaired mitral valve, the anchoring devices may be used to help secure the position of a later-implanted transcatheter mitral valve.

Another aspect of the present disclosure includes methods of anchoring a stented device, such as a valve prosthesis or even a general purpose stent. In such methods, a delivery catheter containing one or more anchoring devices 10 may be maneuvered to the implantation site and may be used to implant an anchoring device 10 in one of the locations previously described herein. The delivery catheter may cause point 26 of anchoring device 10 to penetrate soft tissue to a depth sufficiently shallow to avoid penetrating completely through the smooth muscle of the vascular structure and to avoid placing head 12 of anchoring device 10 flush against the vascular wall in order to prevent impingement into harbor space 40. However, the delivery catheter may also cause point 26 to penetrate to a depth sufficient for edge 28 of mooring feature 24 to grab enough soft tissue to prevent back-out. Once the desired depth has been achieved, the delivery catheter may tug on anchoring device 10 to fully seat the gripping features of anchor 14 and to ensure anchoring device 10 is firmly anchored to the vascular structure.

Alternatively, when the procedure is a V-in-V implantation, the valve prosthesis already implanted in the patient may include a pre-placed anchoring device (not shown), thus obviating the implantation step described above. However, if the previously implanted valve does not already include an anchoring device, anchoring device 10 may be implanted within the existing prosthetic valve in one of the locations described herein in substantially the manner described above.

Once the placement of anchoring device 10 is verified utilizing radiographic imagery, a catheter containing the stented device in a contracted configuration can be guided to the deployment location. Once the catheter is in place, the stented device may be partially or fully deployed, depending on whether the device is resheathable. When the stented device is at least partially resheathable, such as the Portico® valve prosthesis, the stented device may be partially deployed to verify proper location. If not in the desired position, the stented device may be resheathed to make minor positional adjustments. During the resheathing process, care should be taken to avoid snagging the struts of the stented device on the anchoring device 10. The stented device may be fully deployed once any positional adjustments have been made.

During partial deployment or the initial stages of full deployment, the stented device is exposed from within the catheter and expanded so that head 12 of anchoring device 10 passes through an individual cell formed by the struts of the stented device. When full and final deployment is desired, and in order to ensure a firm connection with anchoring device 10, the operator may move the stented device very slightly to ensure a portion of the stent is captured in harbor space 40, thereby prohibiting further migration.

While the method described implants at least one anchoring device 10 prior to delivery of the stented device, an alternative method may reverse this order so that the stented device is implanted prior to the placement of anchoring device 10. In such a method, once the stented device is positioned as desired, point 26 of anchoring device 10 may be inserted through a cell of the stented device and into the vascular structure in substantially the same fashion as previously described. During implantation of the anchoring device 10, care should be taken to avoid puncturing any biological tissue of the stented device that would create an intra-annular or paravalvular leakage pathway.

Figure 11:
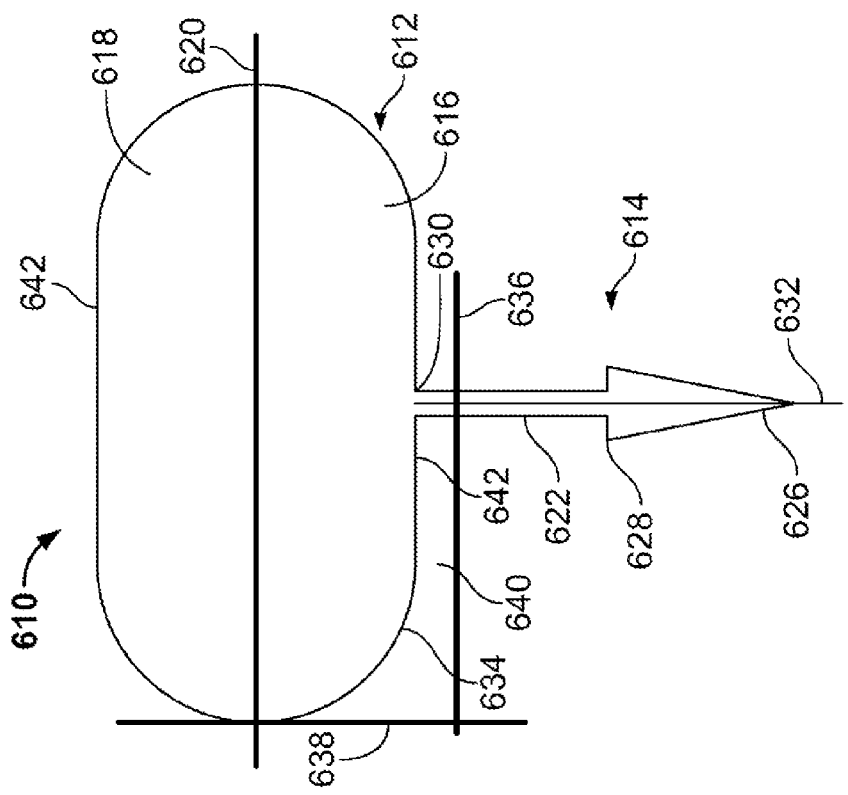
FIG. 11 is a front view of the anchoring device of FIG. 10 defining a harbor space for receipt of a portion of a transcatheter prosthesis.
Figure 10:
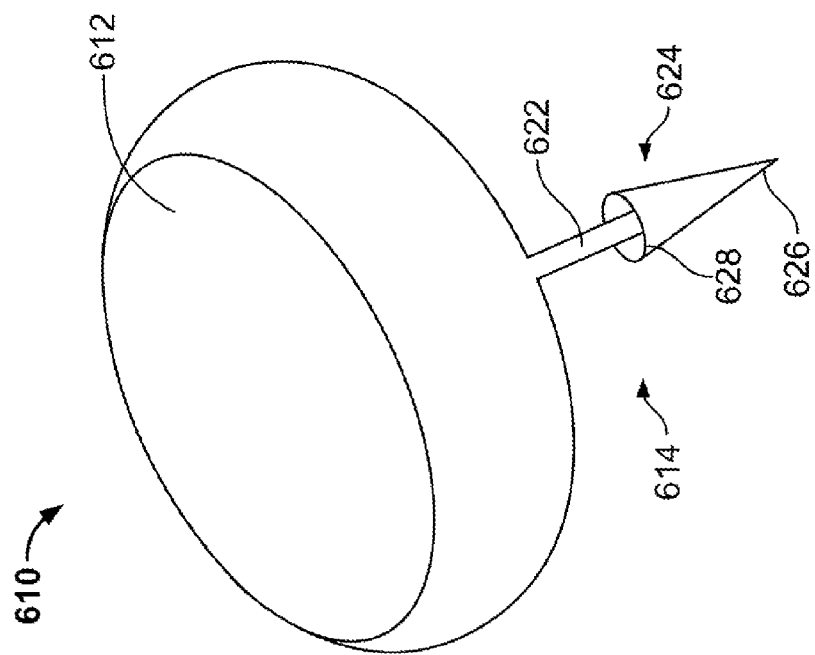
FIG. 10 is a perspective view of an anchoring device having a second embodiment of the head.

FIGS. 10 and 11 illustrate anchoring device 610 in accordance with another embodiment of the disclosure. Anchoring device 610 is similar to anchoring device 10 described above, but differs in the configuration of the head. Head 612 of anchoring device 610 has a flattened or button-like profile with a shape similar to that of an oblate spheroid that includes a flattened top and bottom 642 substantially parallel to a plane defined by an equator 620 of head 610. Equator 620 may separate head 612 first and second sides 616 and 618. Also, a harbor space 640 may be defined by the space between a harbor portion 634 and first and second theoretical planes 636 and 638 as seen in FIG. 11.

While head 612 in FIGS. 10 and 11 is depicted as having a flattened top and bottom 642, this is merely an exemplary depiction. In some embodiments the head may take on the shape of an oblate spheroid without the flattened top and bottom, while in other embodiments the head may have a teardrop or airfoil shape to reduce drag and help maintain laminar blood flow in the area of the head. An airfoil shape may be oriented to provide lift in a direction toward a vascular wall when implanted to assist in maintaining anchoring device 10 in an anchored position within a vascular structure. An anchoring device having such shapes, however, may present challenges with respect to implantation, particularly to ensure that the leading edge of the head faces in the appropriate direction. The head may have various other shapes that would also reduce drag forces, maintain laminar blood flow, and provide a harbor space to anchor a transcatheter valve prosthesis in place without departing from the inventive concept.

Figure 12A:
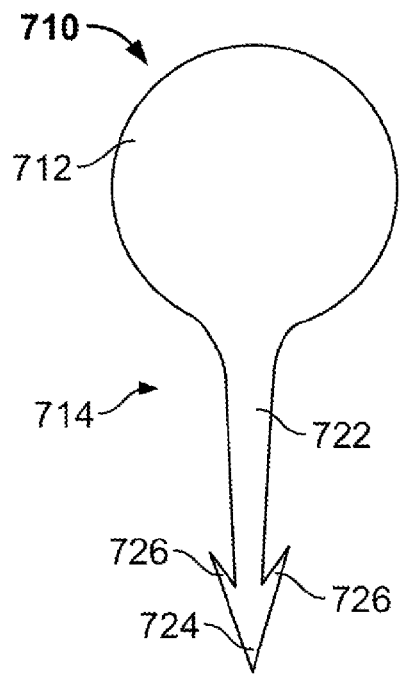
FIG. 12A is a front view of an anchoring device having a second embodiment of the anchor.
Figure 12B:
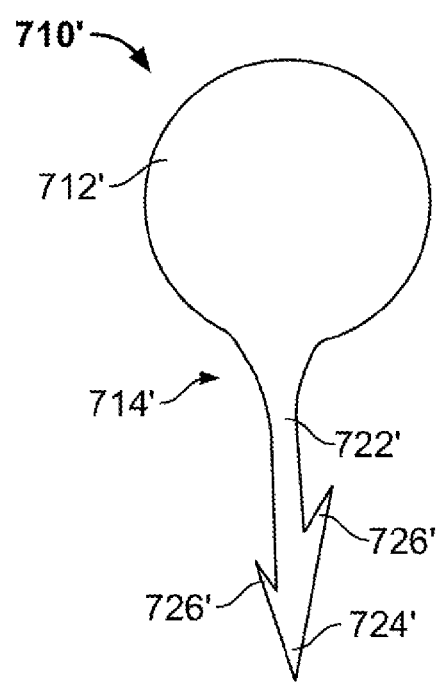
FIG. 12B is a front view of an anchoring device having a third embodiment of the anchor.

FIGS. 12A and 12B depict other embodiments of an anchoring device in accordance with the present disclosure, but differing in the configuration of the anchor. FIG. 12A shows anchoring device 710 having an anchor 714 with a shaft 722 that terminates at a sharpened point 724 at one end. Shaft 722 may also include a barb 726 projecting away from shaft 722 and from point 724 in order to prevent back-out when anchor 714 has been implanted into a vascular structure. Shaft 722 may include one barb 726 or a plurality of barbs 726 in order to spread the gripping action over a larger area. When shaft 722 includes a plurality of barbs 726, each barb 726 may be disposed at substantially the same position along the length of shaft 722, as seen in FIG. 12A. Alternatively, barb 726' may be displaced from one another along the length of shaft 722', as seen in FIG. 12B. Just as with anchor 14 of anchoring device 10 described above, shafts 722 and 722' may be tapered and may have a length that prevents anchors 714 and 714' from completely penetrating the musculature of the vascular structure.

Figure 13A:
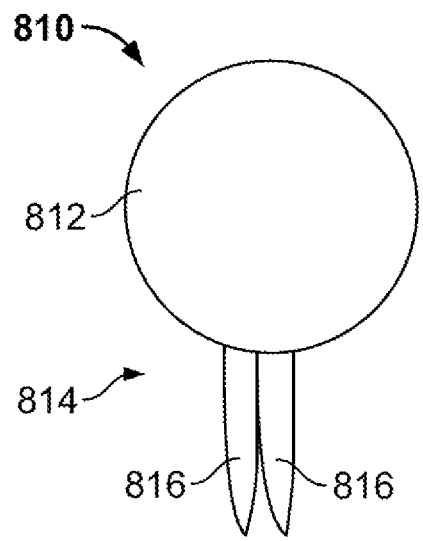
FIG. 13A is a front view of an anchoring device having a fourth embodiment of the anchor in a first position.
Figure 13B:
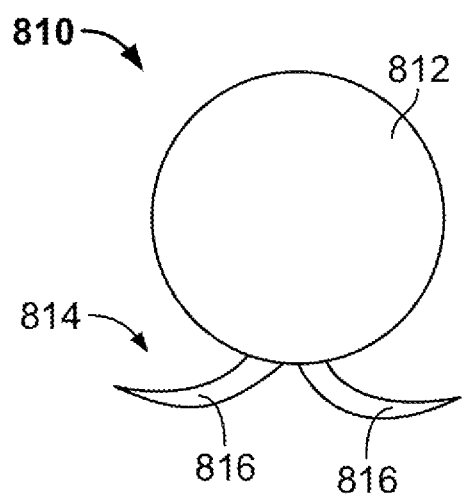
FIG. 13B is a front view of the anchor of 13A with the anchor in a second position.

FIGS. 13A and 13B illustrate yet another embodiment of an anchoring device which also differs from anchoring device 10 in the configuration of the anchor. Anchor 814 may include a plurality of splaying arms 816. Each of arms 816 may have one end connected to a first side of head 812, and another end sharpened to penetrate soft tissue. As shown in FIG. 13A, arms 816 may have a first position in which they extend from head 812 generally along a longitudinal axis. Arms 816 may be flexible and may be made from memory metal with a natural bias toward outward expansion such that, when arms 816 penetrate soft tissue, they splay outwardly as shown in FIG. 13B, thereby securing anchoring device 810 into the soft tissue to prevent back-out.

While certain embodiments of the head and anchor have been depicted herein, any shape of head and any anchor sufficient to attach to tissue that provides an abutment surface for a stent may be utilized without departing from the scope of the present disclosure.

Another aspect of the present disclosure includes anchoring devices that may be utilized in a V-in-V configuration. Such devices, as further described below, may be affixed to an inner portion of an annuloplasty ring or an inner portion of a prosthetic valve, such as a cuff, so that a later implanted stented device may have an anchoring support to prevent migration.

Figure 14A:
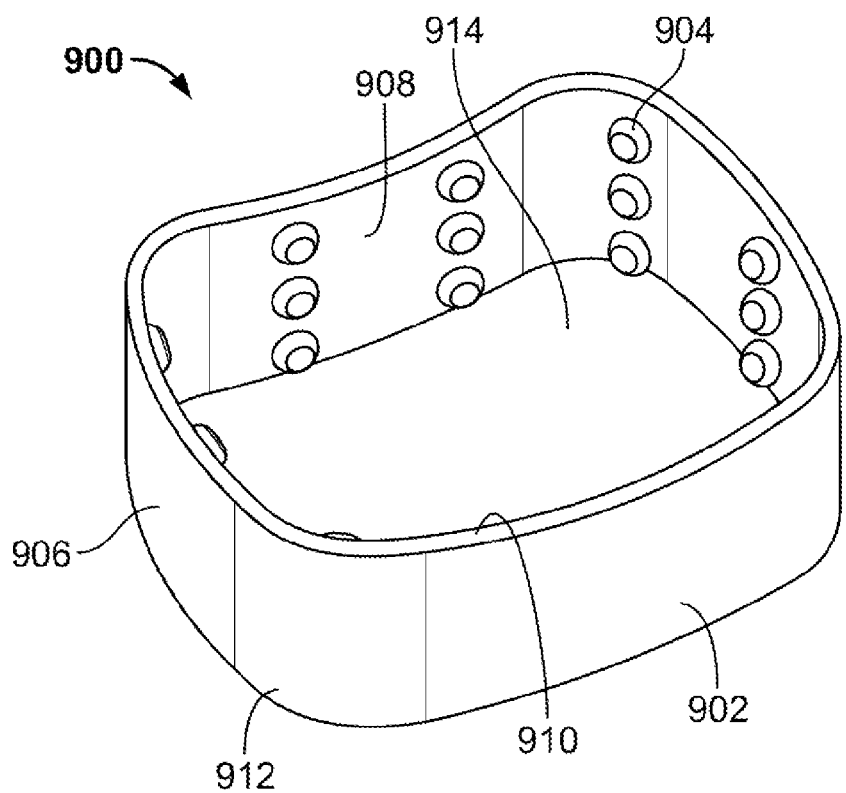
FIG. 14A is a perspective view of an anchoring sleeve according to another aspect of the disclosure.
Figure 14B:
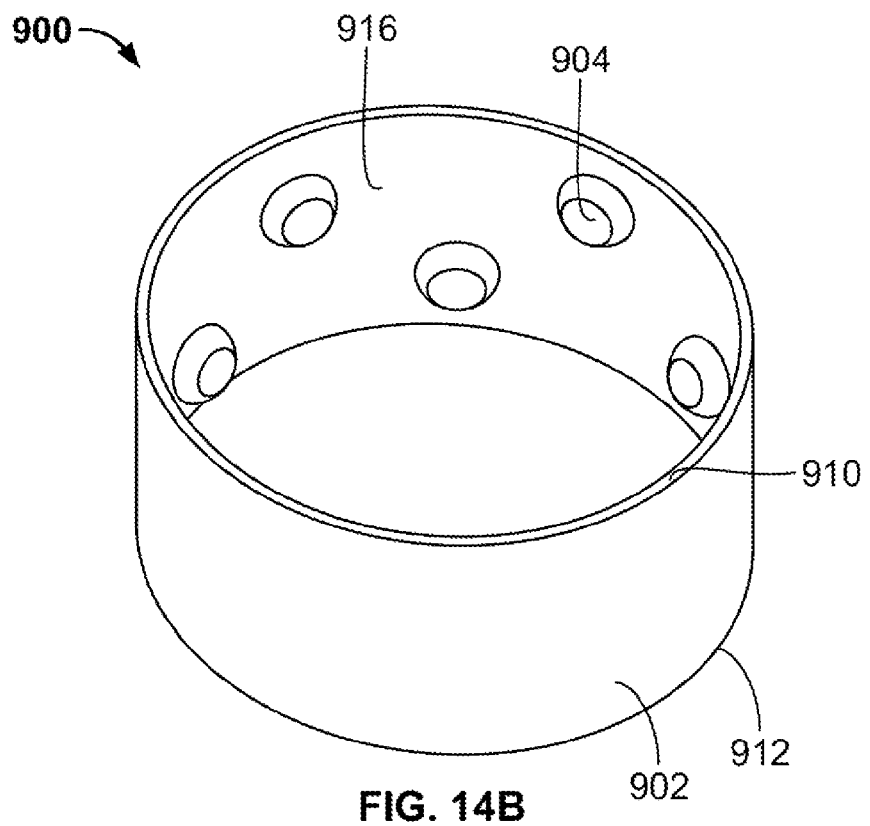
FIG. 14B is a perspective view of another example of an anchoring sleeve.

FIGS. 14A and 14B depict an anchoring sleeve 900 that generally includes a sleeve body 902 and a plurality of nodules 904. The sleeve 900 may include an outer surface 906, an inner surface 908 and a thickness defined therebetween. The sleeve 902 may also include a first end 910, a second end 912 and a width defined therebetween. The sleeve 900 can be configured in an annular arrangement so as to define an open area 914 that extends therethrough. The particular shape of sleeve body 902 may be configured for attachment to a prosthetic valve in order to conform to the inner geometry of the prosthetic valve and to make use of any usable portion of the prosthetic valve where attachment thereto would not interfere with valvular functions. For example, anchoring sleeve 900 as shown in either FIG. 14A or 14B may be selected to attach to an inner region of a prosthetic valve, for example an annulus section of a transcatheter valve, in a position where such attachment would not interfere with the functioning of the leaflets or block any sinus areas or openings within the valve.

Attachment may be achieved by sewing the anchoring sleeve 900 to an inner portion of a prosthetic valve generally within the inflow region. Such inner portion may include a cuff, for example, with which the sleeve body 902 can be sewn. Other forms of attachment of anchoring sleeve 900 to a prosthetic valve are also possible, including using adhesives or mechanical structures such as hooks, clips, or the like.

The cross-sectional profile of the anchoring sleeve 900 may have various configurations that may be selected for conformance to an inner profile of a prosthetic valve. For example, where the inner profile of a prosthetic valve is triangular due to a tri-leaflet construction, the anchoring sleeve 900 may have a similar triangular profile to match that of the prosthetic valve. Similarly, where the inner surface to which the anchoring sleeve 900 may be attached has a circular profile, the anchoring sleeve may have a circular profile.

The sleeve 902 may be constructed from various materials that may provide flexibility and durability. Some examples of the various materials that may be utilized are filamentary materials woven into a sleeve 902 such as, but not limited to, polyester, polyethylene (including ultra-high molecular weight polyethylene (UHMWPE)), polytetrafluorethylene (including expanded polytetrafluorethylene), nylon, polypropylene, aramids (such as Kevlar-based materials), polydioxanone, polygycolic acid, liquid crystal polymer (LCP), organic material (silk, animal tendon, or the like), or any combination of these materials. Alternatively, the sleeve 902 may molded or otherwise formed into a unitary structure from a polymeric material or a metallic material, such as Nitinol, titanium, stainless steel, or cobalt-chromium, for example. The sleeve 902 may include radiopaque markers, such as platinum or barium, for radiographic locational placement.

A nodule 904 may be a hemispherical, cylindrical, or other shaped protrusion that extends from the sleeve inner surface 908. These nodules 904 may be formed from the same material as the sleeve 902 and formed together as a unitary structure with the sleeve 902, or nodule 904 may be a separate component and made from a polymeric or metallic material, such as Nitinol, titanium, stainless steel, or cobalt-chromium, for example, and affixed to sleeve 902. Each nodule 904 may include an eyelet (not shown in FIG. 14A or 14B) for sewing the nodule 904 to the sleeve 902. Alternatively, the nodule 904 may be affixed to the sleeve 902 by an adhesive or by sonic welding, for example.

A plurality of nodules 904 may be affixed to the sleeve 902 in a number of different patterns and may be provided in various sizes. In one example, the nodules 904 may be arrayed radially and longitudinally in various patterns as illustrated in FIGS. 14A and 14B. In another example, the nodules 904 may be radially arrayed and reside in a single plane (not shown). Larger diameter nodules 904 may be better suited for stents having large stent cells or for a section of a stent having large stent cells. However, smaller nodules 904 may be well suited to fit within both small and large stent cells. For example, where a second replacement valve includes large stent cells, two or more nodules may fit within the cells. Where a sleeve includes a plurality of nodules 904, the spacing of these nodules 904 with respect to one another may be predetermined to correspond to the stent design so that each nodule may extend into an individual stent cell without interfering with the expansion of the stented device.

Nodules generally operate by forming channels 916 between adjacent nodules 904. A stent may be inserted into the aperture and expanded such that various nodules 904 extend through the individual cells of a stented device and the struts forming those cells reside within the channels 916. The nodules 904 may be constructed to have an overhang (not shown) to form a harbor space similar to that previously described herein, or the nodules 904 may have a constant diameter or be tapered or rounded so that no overhang and no harbor space is formed. Similar to anchoring device 10, the nodules 904 may act as a barrier or a back-stop to the struts of a stent to prevent longitudinal migration of a later implanted stented device.

Anchoring device 10 and nodules that provide a harbor space (not shown) may be advantageous in that they may prohibit a stent from migrating in a longitudinal direction and from movement in a transverse direction over the head of the anchoring device 10 or nodule 904 in order to prevent jump-over of the anchoring device 10 or nodule. As such, only one or two of these anchors 10 or nodules may be utilized, which may be particularly advantageous where anchoring device 10 is implanted in vivo.

Jump-over may occur where, perhaps by the beating of the heart, a strut moves in a transverse direction beyond the boundary of the nodule 904 and then moves longitudinally to pass over the nodule 904. Prevention of jump-over may be achieved by providing a harbor space with an overhang, as previously described herein, to prevent movement in the transverse direction. Prevention of jump-over may also be achieved by targeting longitudinal movement of the stent over the nodule 904 rather than transverse movement. Such longitudinal movement can be prevented by locating a nodule 904 on the inner surface 908 of the sleeve 902 opposite another nodule 904. Thus, any transverse movement away from one nodule 904 will be in the direction of the other nodule 904, which would still be able to perform the function of blocking longitudinal movement. Thus, nodules 904 that form a channel 916, but not a harbor space, may be helpful in prohibiting migration in a longitudinal direction and also prohibiting jump-over by locating multiple nodules 904 at various locations along the inner surface 908 of the sleeve 902.

Additionally, nodules that form a channel 916, but not a harbor space, may be advantageous where a later implanted transcatheter valve is resheathable. As has just been described, such a nodule may not prevent transverse movement, which may be beneficial for ease of resheathing from a point where the struts of the transcatheter valve reside within the channels 916.

Figure 15:
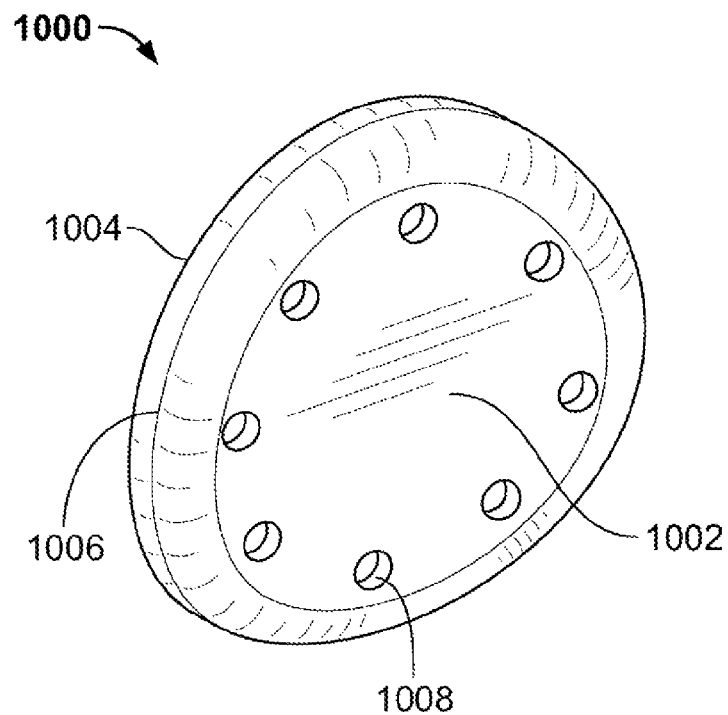
FIG. 15 is a perspective view of an anchoring element that can be used in connection with the anchoring sleeves of FIGS. 14A and 14B.

FIG. 15 shows an anchoring element that may be an alternative or supplement to the anchoring sleeve 900 and may be utilized, for example, where a lower profile is desirable. The anchoring element, as shown in FIG. 15 may be in the form of a disc 1000 that may be somewhat saddle-shaped along an axis thereof so as to match the rounded profile of the inside surface of a corresponding prosthetic valve. The disk 1000 can include an inside surface 1002 and an outside surface 1004 that can be spaced apart to define a thickness of the disc 1000. A sidewall 1006 can extend between the inside surface 1002 and the outside surface 1004. In an example, the disc 1000 can be of a thickness such that sidewall 1006 extends far enough away from a junction between the disc 1000 and the inside surface of the prosthetic valve that disc 1000 alone can act as an anchoring feature. In such an example, sidewall 1006 can form an undercut such that a harbor space (not shown) is present therein that can capture a portion of a stent therein, as described above. In other instances, sidewall 1006 can be generally perpendicular to adjacent portions of inside surface 1002 and/or outside surface 1004 to abut a portion of a stent to prevent migration thereof in a manner similar to the nodules 904 discussed above with respect to FIGS. 14A and 14B.

Disc 1000 can include a plurality of attachment holes 1008 therein, such as around a periphery thereof, as shown. The attachment holes 1008 can be used to attach disc 1000 to various portions of a prosthetic valve assembly or other valvular prosthesis, such as by sewing the disc via suture to the prosthesis through the attachment holes. Attachment may be achieved in various other ways such as stapling or clipping the disc to the prosthesis, for example. Examples of the various attachment locations can be found in FIGS. 5-9 as previously described herein in relation to anchoring device 10. In another example, a plurality of discs 1000 can be sutured or otherwise attached to a sleeve, such as sleeve 902 in FIGS. 14A and 14B. A variation of a disc can be similar to disc 1000 but without any attachment holes 1008, which can be attached in a desired location using adhesives or the like.

In another example, disc 1000 can act as a mounting feature for an individual nodule (not shown in FIG. 15) that can be similar to those of anchoring sleeve 900. In such an example, the nodule can be sized to be positioned between the peripheral attachment holes 1008 and can extend from inside surface 1002. The nodule can be affixed to disc 1000 by adhesives, by a hook-and-eye style attachment or by other means. A configuration of this type can allow for attachment of one or more discs 1000 within a prosthesis for implantation. Subsequently, corresponding nodules can be attached thereto to act as anchoring features for another prosthesis (such as in a V-in-V procedure) implanted subsequent to the first prosthesis in the same procedure in which nodules are installed.

Figure 16A:
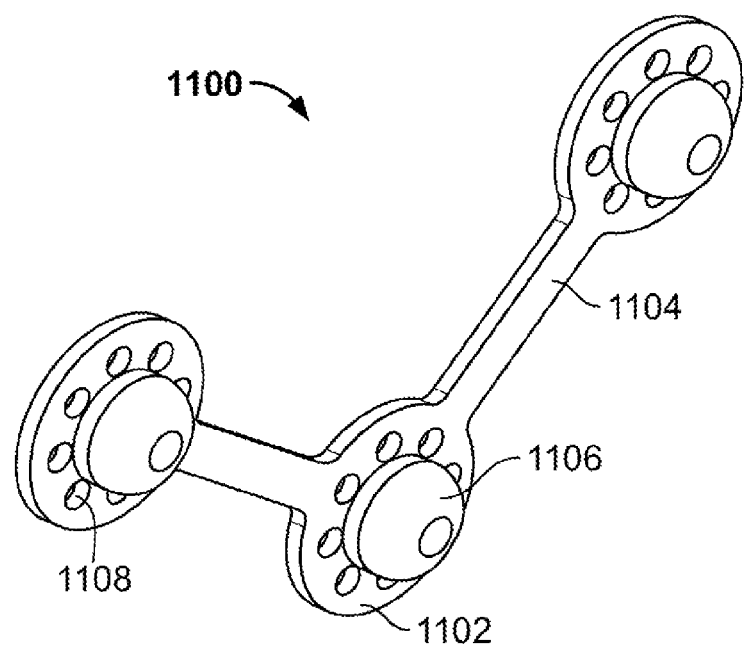
FIGS. 16A and 16B are perspective views of an anchoring apparatus according to another aspect of the disclosure.
Figure 16B:
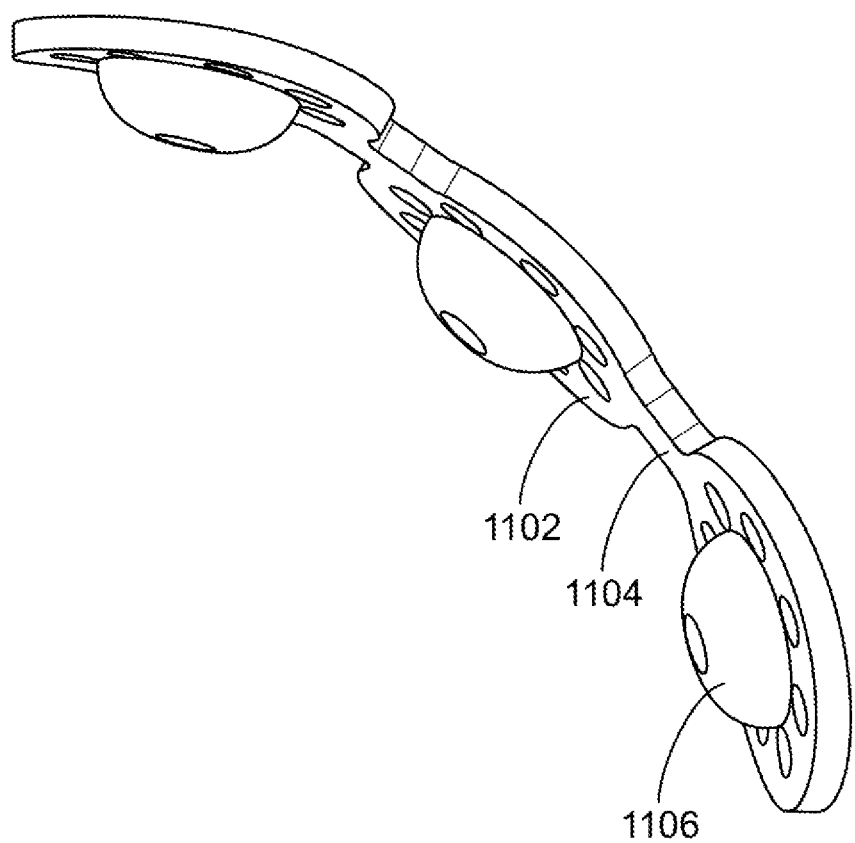
Figure 16C:
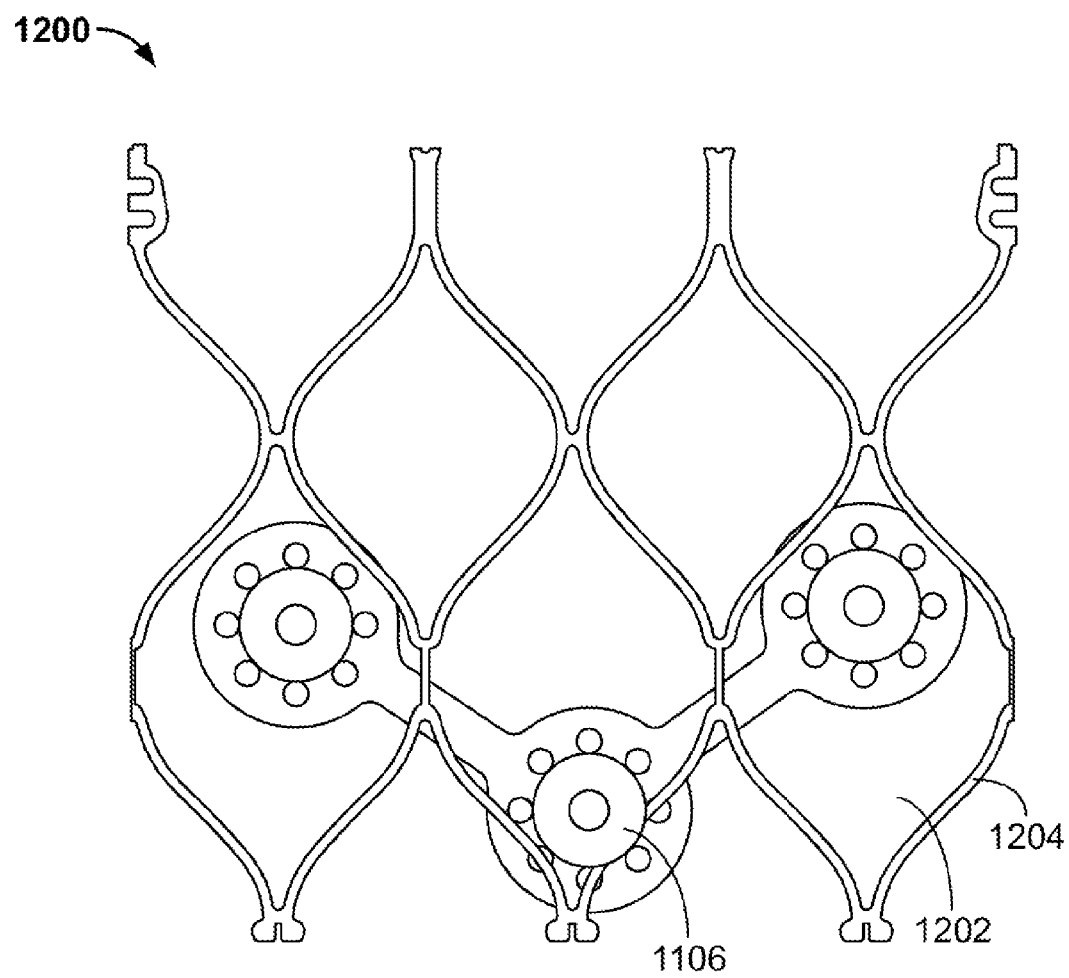
FIG. 16C is a side view of the anchoring apparatus of FIG. 16A depicting potential interaction between the anchoring apparatus and a stented device.

As shown in FIG. 16A-C, an anchoring apparatus 1100 can include a plurality of attachment discs 1102 connected together in a predetermined pattern or other spatial relationship by one or more connector arms 1104. Attachment discs 1102 may be the same as discs 1000 previously described or may be relatively thin discs as compared to discs 1000 and act as an attachment interface between a nodule 1106 and the prosthetic valve. The nodule 1106 may be the same as those included in the anchoring sleeve 900. The attachment disc 1102 may have a larger diameter than a nodule 1106.

The attachment disc 1102 and nodule 1106 may be constructed as a unitary structure or may be separate structures attached together by mechanical means such as welding, adhesive, interference-fit or threaded connection. As the attachment disc 1102 may have a larger diameter than the nodule 1106, the attachment disc 1102 may have a portion that extends beyond the nodule 1106. This portion may include attachment apertures 1108 that extend through the attachment disc 1102 to provide for a threaded connection or other type of connection with the prosthetic valve.

Multiple attachment discs 1102 and nodules 1106 may be attached in various configurations by the connector arm 1104. The connector arm 1104 and attachment discs 1102 can be bent, as illustrated by FIG. 16B, to conform to an inner surface of a valvular prosthesis. The connector arms 1104, attachment discs 1102, and nodules 1106 may all be formed as a unitary structure or, alternatively, the connector arms 1104 may be mechanically joined to multiple attachment discs 1102.

The anchoring apparatus 1100 can be attached within a valvular prosthesis to provide anchoring features therein for a stented device, such as that depicted in FIG. 16C, to be implanted therein (such as in a subsequent V-in-V procedure), in a manner similar to the attachment sleeve 902, discussed above. The later implanted stented device 1200 may be expanded within the valvular prosthesis such that a nodule 1106 extends through a cell 1202 formed by individual struts 1204. The nodules 1106 may act as a backstop or an abutment surface to oppose migration of the stented device 1200 as depicted in FIG. 16C.

Further, the various anchoring devices shown in FIGS. 14A, 14B, 15, and 16 can also be attached within an anchoring stent that can be similar to any of the various stent shown herein (such as stent 100 in FIG. 3B) without a prosthetic valve structure attached therein. In one example an anchoring sleeve 902, such as those shown in FIGS. 14A and 14B can be sutured directly to a stent structure without any prosthetic valve present. Such an anchoring stent can be configured to be crimped to a low-profile (e.g. about 10 French) for implantation to a surgical site, such as within an aortic annulus. In the same procedure, valve prosthesis, including a stent and a prosthetic valve structure can be implanted therein and can engage the anchoring features provided by the anchoring stent such that migration thereof can be prevented. Because of the presence of two stents in such a structure, the thickness of the material in both of the stents can be reduced relative to those used in a single-stent valvular prosthesis. Accordingly, the inner valvular prosthesis can be configured to be crimped to a relatively low-profile (e.g. less than 16 French). Such configurations can make transcatheter delivery thereof and more feasible among a wider selection of patients.

While the above disclosure has described certain heads in relation to particular anchors, these are merely examples. Any combination of a head and an anchor that can form a harbor space or radially extending surface to receive or abut a stented device may be achieved without departing from the spirit of the present invention.

The invention claimed is:

1. A valvular prosthesis for use within a cardiovascular structure, comprising:
 a prosthesis having an outer portion for engagement with the cardiovascular structure and an inner portion disposed opposite the outer portion; and
 an anchoring device having a plurality of disc-shaped members and a plurality of nodules, the disc-shaped members each having first and second end surfaces and a side surface spanning therebetween, each of the disc-shaped members being connected to an adjacent disc-shaped member via a connector arm that extends from the side surfaces thereof, the plurality of nodules each projecting from the first end surface of a respective one of the disc-shaped members, and the second end surfaces of the disc-shaped members being engaged with the inner portion of the prosthesis.

2. The valvular prosthesis of claim 1, wherein the prosthesis is a bioprosthetic valve including a cuff and a plurality of leaflets.

3. The valvular prosthesis of claim 2, wherein the disc-shaped members each include apertures that extend through the first and second end surfaces thereof, the disc-shaped members being sewn to one of the cuff or at least one of the plurality of leaflets via the apertures.

4. The valvular prosthesis of claim 1, wherein the prosthesis is an annuloplasty ring including a core disposed between the inner portion and outer portion.

5. The valvular prosthesis of claim 4, wherein the disc-shaped members are sewn to the inner portion of the annuloplasty ring.

6. A method of anchoring a stented device, comprising:
 guiding a catheter to a deployment location within the cardiovascular system of a patient, the catheter having contained therein, in a contracted configuration, an expandable stented device including a plurality of cells, the deployment location including at least one anchoring device with a head projecting radially inwardly within the deployment location, the head having a rounded body with at least two surfaces that meet each other at a common plane;
 removing the stented device from the catheter at the deployment location;
 expanding the stented device such that the head of the anchoring device extends through one of the cells of the stented device;
 at least partially contracting the stented device after the expanding step;
 adjusting the stented device along the deployment location after the step of at least partially contracting the stented device to reposition the stented device relative to the head; and
 re-expanding the stented device after the adjusting step so that the head extends through another one of the cells of the stented device.

7. The method of claim 6, wherein the anchoring device further has a first portion penetrated into tissue within a vascular structure, the head being attached to the first portion, and the head and the tissue together at least partially defining a harbor space.

8. The method of claim 7, further comprising moving the stented device in a direction with or against the direction of blood flow, such that a strut of the stented device is received within the harbor space, thereby obstructing further movement of the stented device.

9. The method of claim 6, wherein the anchoring device is attached to a valvular prosthesis already present within the deployment location.

10. The method of claim 8, further comprising deploying an anchoring stent including the anchoring device within the deployment location prior to the removing step.

* * * * *